United States Patent [19]

Bukta

[11] Patent Number: 5,709,205
[45] Date of Patent: Jan. 20, 1998

[54] PULSOXIMETRY SENSOR

[75] Inventor: Anton Bukta, Sindelfingen, Germany

[73] Assignee: Hewlett-Packard Company, Palo Alto, Calif.

[21] Appl. No.: 501,384

[22] Filed: Jul. 12, 1995

[30] Foreign Application Priority Data

Aug. 23, 1994 [DE] Germany .................. 44 29 845.5

[51] Int. Cl.[6] ......................................... A61B 5/00
[52] U.S. Cl. ............................... 128/633; 128/690
[58] Field of Search ........................ 128/633, 632, 128/665, 664–667, 680, 690

[56] References Cited

U.S. PATENT DOCUMENTS

| | | |
|---|---|---|
| 4,685,464 | 8/1987 | Goldberger et al. . |
| 4,865,038 | 9/1989 | Rich et al. . |
| 5,090,410 | 2/1992 | Saper et al. ............... 128/633 |
| 5,209,230 | 5/1993 | Swedlow et al. .......... 128/644 |
| 5,311,865 | 5/1994 | Mayeux . |
| 5,351,694 | 10/1994 | Davis et al. ............... 128/672 |
| 5,438,986 | 8/1995 | Disch et al. ............... 128/633 |
| 5,490,523 | 2/1996 | Isaacson et al. .......... 128/633 |
| 5,551,423 | 9/1996 | Sugiura .................... 128/633 |

FOREIGN PATENT DOCUMENTS

| | | |
|---|---|---|
| 481 612 | 9/1991 | European Pat. Off. . |
| 572 684 | 5/1992 | European Pat. Off. . |
| 37 03 458 | 2/1987 | Germany . |
| 37 23 880 | 7/1987 | Germany . |

*Primary Examiner*—John P. Lacyk

[57] ABSTRACT

Pulsoximetry sensor with two sensor elements, which are fixed to a support body, which has fastenings for the sensor elements interconnected by means of a web, so that the two sensor elements can be placed on opposite sides of the hand or foot.

12 Claims, 3 Drawing Sheets

PULSOXIMETRY SENSOR

FIELD OF INVENTION

The present invention relates to a pulsoximetry sensor for the foot or hand for measuring oxygen saturation in the blood of a patient according to the preamble of the main claim.

BACKGROUND ART

Pulsoximetry is a known, standard method for the non-invasive measurement of blood. Light is irradiated into the tissue of a patient with a least two wavelengths and conclusions are drawn concerning the oxygen saturation from the attenuation of the a.c. component of the reflected or transmitted signal. Typically light-emitting diodes and photocells are used for this purpose. Body parts particularly suitable for the measurement are the fingers or toes and then the photocells can be applied relatively closely to the skin without any tilting, so that the a.c. component of the signal, which is much smaller than the constant component thereof can be detected as well as possible.

In the case of newborn, high-risk babies, where the oxygen supply is a critical parameter, normally measurements take place on the hand or foot an in certain cases on the thumb, because the fingers are too small for applying a sensor.

U.S. Pat. No. 4,685,464 discloses a finger sensor, in the which the sensor elements are fixed to a support, which in much the same way as a clothes peg consists of two legs, which are interconnected by means of a spring clip, so that the sensor elements are held in position on the finger. EP 481 612 A1 describes a finger sensor in which the finger to be measured is placed on a support, which has the first sensor element and then the second sensor is fixed by means of an adhesive tape to the finger and support. The finger sensor according to U.S. Pat. No. 4,865,038 comprises flat, sandwich-like elements, which are interconnected and can be placed round the finger, so that the sensor elements can be brought into facing positions.

DE 37 03 458 A1, U.S. Pat. No. 5,311,865 and EP 572 684 A1 finger sensors are known, which have a support body into which is inserted the finger. Whereas in DE 37 03 458 A1 the support body simultaneously contains the sensor elements as fixed integrated components, in the case of the sensors of U.S. Pat. No. 5,311,865 and EP 572 684 A1 the sensor elements are placed in an additional band, which is placed round the finger tip, to which the support is fixed.

DE 37 23 880 A1 shows the fastening of an optoelectronic device for radiating through living tissue with an adhesive closure for fixing to a finger or toe, which is positioned transversely to the cap embracing the finger or toe tip.

In all these known sensors in practice problems have been encountered in connection with the fixing and when applying components to be accurately positioned with respect to the same. Due to the large number of components certain of the known sensors are also relatively disadvantageous with regards to reusability and the consequently necessary cleanability and sterilisability. Due to their construction and size other known sensors are unsuitable for use with newborn babies. A typical detachability is disadvantageous, if checks have to take place a short intervals with a newborn baby having sensitive skin and as a result skin irritations occur. This is particularly so if the sensor is used with an adhesive plaster, where the sensor elements are fitted to said plaster beforehand. In order to apply these sensors it is necessary for the sensor elements (transmitter and receiver to be accurately positioned with respect to one another. With this fastening principle this leads to the important disadvantage that the user has the transducer already adhering to the skin and must be removed again in certain circumstances if the sensor fails to provide reliable measurements. Thus, the accurate positioning is frequently problematical with such sensors. Another disadvantage is the increased amount of waste produced.

The problem of the present invention is therefore to propose a pulsoximetry sensor, which can be rapidly and simply fixed and removed and which is also suitable for newborn babies.

SUMMARY OF THE INVENTION

In accordance with the invention mounting supports or fastenings for sensor elements of pulsoximetry sensor have a depression in which the particular sensor element is located. The sensor element can be moulded in epoxy resin and is held in the depression by corresponding friction between the depression wall and the sensor element housing. The connecting cables or leads of the sensor elements are passed out of the depression through corresponding openings. They can in turn either be provided with a notch or a hole, whereby in the case of the latter firstly the cable is passed through, then the components are soldered and finally epoxy resin is moulded round it. This is necessary so that the unit formed by the sensor element and cable provides an absolutely tight connection, so that the unit can be immersed in liquids for disinfecting purposes. The web connecting the two fastenings is arcuately constructed, so that the fastenings with the sensor elements are held facing one another. Thus, for measurement purposes the sensor is applied to the foot or hand, the sensor elements facing one another as a result of the sensor shape, and are held at the desired position. Fixing takes place by means of a flexible clip shaped onto the first fastening and which is guided via the second fastening, being detachably securable to the fastening or web as a function of the thickness of the body part. The flexible clip and the curved web are oriented in the same direction, so that the support body can laterally engage on the foot or hand and is held by the clip spanning the foot or hand. Using the other hand the flexible clip is placed over the organ and secured. Fixing can take take place either directly on the fastening or on the web by means of suitable clamping connections.

A sensor constructed in this way requires no additional fixing mean, which greatly reduces the amount of garbage in clinics and permits a rapid fitting and removal, which is very important particularly in the case of newborn babies. As a result of the preshaped support body an incorrect positioning of the sensor elements is largely avoided and application is greatly facilitated, because the support body is already applied round the body part. In addition, the sensor permits an easy and rapid checking of the measurement point. Further advantageous developments can be gathered from the subclaims.

According to a preferred embodiment on the top of the fastening and/or the web is provided at least one recess in which can be placed the clip and which holds the latter in position. This can be brought about by a correspondingly shaped recess, which clamps the clip in the fastening. The security of the connection can be increased by corrugations shaped onto the clip, so that a frictional clamping connection is obtained, which prevents any unintentional detachment of the sensor from the organ.

According to another embodiment on the top of the fastening are provided two displaced recesses on both facing edges of the depression, so that the clip is held in position by a clamping action.

Preferably the recesses have a dovetail-like cross-section, so that an upward displacement of the clip is prevented.

According to another preferred embodiment the clip is laterally corrugated, in order to bring about a friction action between the clip and the recess, so that the clip is securely held in position.

According to a further development the clip is corrugated on the top and/or bottom and is passed through at least one ring holding the clip in its position on the edge of the depression. During fixing it is necessary to thread the clip into the corresponding ring.

According to another variant on the fastening or web is provided a detent in which engages the clip with corresponding locking openings. Through a plurality of openings in the web it is possible to bring about an individual adaptation to the organ size.

The one-piece support body is advantageously made from silicone, which on the one hand has corresponding skin compatibility and on the other a softness, which on fixing the clip in the recesses gives an advantagous connection, which in the above-described manner prevents unintentional detachment and at the same time can be rapidly fitted and removed. The invention is described in greater detail hereinafter relative to non-limitative embodiments and the attached drawings.

DETAILED DESCRIPTION OF THE DRAWING

The drawings individually show the different pulsoximetry sensors with their support bodies. With the exception of FIG. 1a the sensor elements 2 are not shown so as not to overburden the representation.

Figure 1A:
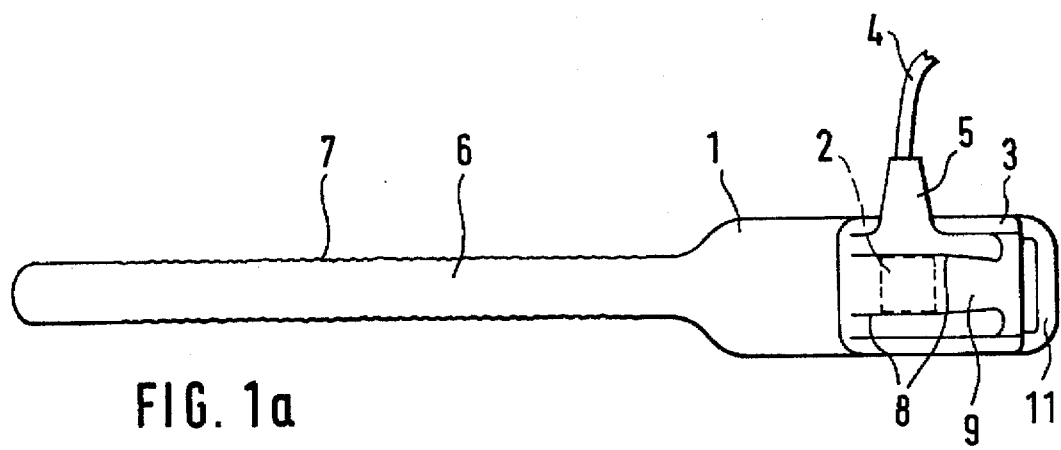
FIG. 1 A pulsoximetry sensor with a support body on which is shaped a clip with lateral corrugations.

In FIG. 1a shows the underside of a support body 1 with the sensor elements 2 is illustrated as being arranged in the lower mounting support or fastening 3 and whose connecting cable or lead 4 is passed through a correspondingly shaped hose liner 5, which is provided with an opening. Onto the fastening 3 is shaped a clip 6 extending away to the left and which on the lateral edge has corrugations 7 with which the clip 6 can engage with the side walls 8 of the recess 9 of the facing upper mounting support or fastening 10 shaped correspondingly to the mounting support or fastening 3. On the end face of the support body 1 is located on the web 14 an additional ring 11 into which can be inserted the clip 6 for securing purposes.

Figure 1B:
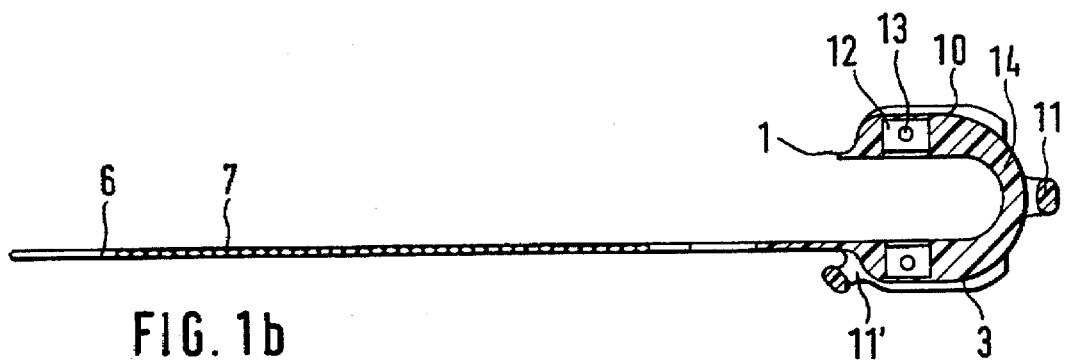

In FIG. 1b is illustrated a longitudinal section through the support body 1 with the lower fastening 3, the upper fastening 10, the ring 11, the clip 6 with the corrugation 7 and the depression 12 for receiving the sensor elements 2. The opening 13 in the depression 12 is used for the passing of the cable 4 through the hose liner 5. In this embodiment here is an additional ring 11' in the vicinity of the fixing of the clip 6.

Figure 1C:
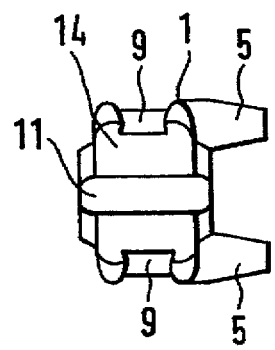
Figure 1D:

In FIG. 1c is illustrated the end face of the support body 1 with the hose liners 5, the ring 11 and the recesses 9 on the lower fastening 3 and the upper fastening 10. As is again illustrated in FIG. 1d, the recess 9 has dovetail-shaped construction, so that the clip 6 with its corrugation 7 on the lateral edge is securely held in position as a result of the clamping an frictional action.

In place of the hose liner 5 with opening 13 the lead 4 with the sensor element 2 can also be inserted in a correspondingly shaped recess or notch which holds the lead in position. The sensor element 2 is then fixed in position by the side walls of the depression.

In the case of the support body shown in FIG. 1 the fastenings 3 an 10 are connected by means of the arcuate web 14, so that it brings the two fastenings into a directly superimposed position when in its basic position and as a result the sensor elements are in the correct position for the measurement.

Figure 2A:
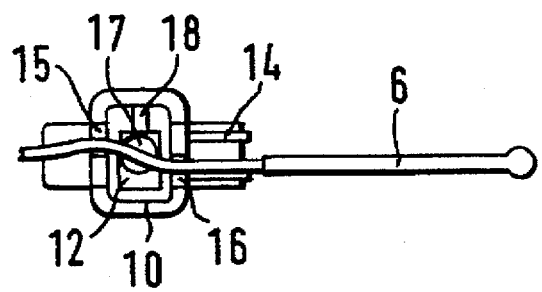
FIG. 2 Another embodiment of a sensor with a support body, in which the clip is clamped in sloping manner on the fastening.
Figure 2B:
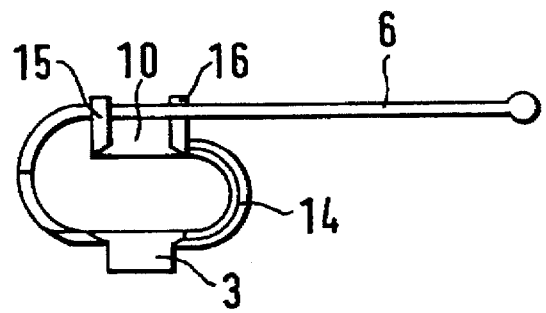

In FIG. 2 is shown a correspondingly designed support body 1, in which the clip 6 is retained by two displaced recesses 15 and 16 on the upper fastening 10. FIG. 2a is a plan view of the support body 1 with a clip having a round cross-section. The depression 12 is used for receiving the sensor body and the opening 17 constitutes a light exit aperture. The cable of the sensor element is led out via the notch 18. The side view of FIG. 2b also shows the preshaped retention of the web 14, which brings the two fastenings 3 and 10 into a superimposed position.

Figure 3A:
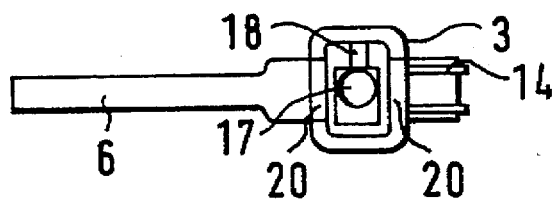
FIG. 3 Another embodiment of a sensor with a support body, in which the top of the clip is corrugated.
Figure 3B:
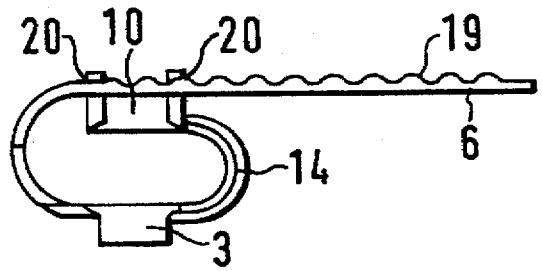

The embodiment of FIG. 3 shows in FIG. 3a the underside of the support body 1 with a clip 6, which is provided on its top with corrugations 19, which must be passed through corresponding rings 20 on the upper fastening 10 for secure fixing purposes. This can be gathered from FIG. 3b, which is a side view of the support body 1 with drawn in clip 6.

Figure 4A:
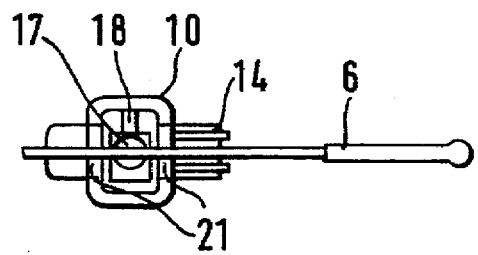
FIG. 4 A sensor with a support body in which the clip is secured in s recess with clamping jaws.
Figure 4B:
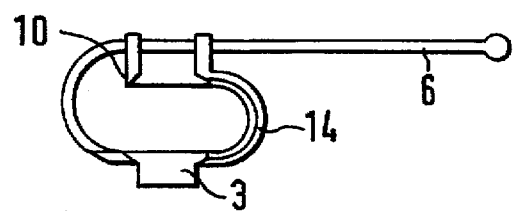
Figure 4C:
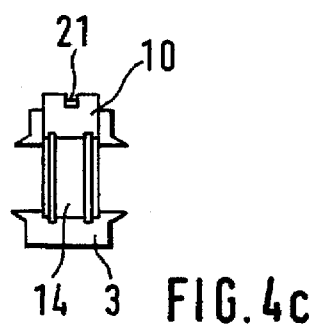

In the case of embodiment shown in FIG. 4 the clip 6 having a round cross-section is held in recess 21, which is so constructed that it laterally secures the clip. FIG. 4a is a plan view, FIG. 4b a side view and FIG. 4c the end view of the support body 1. In FIG. 4c the clip 6 is not in the recess, unlike in FIGS. 4a and 4b.

Figure 5A:
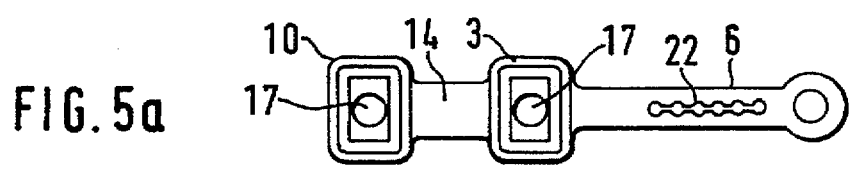
FIG. 5 A sensor with a support body having locking openings for receiving a corresponding detent.
Figure 5B:
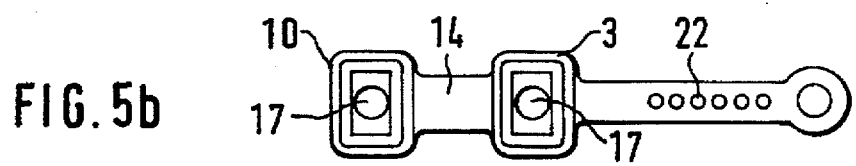
Figure 5C:
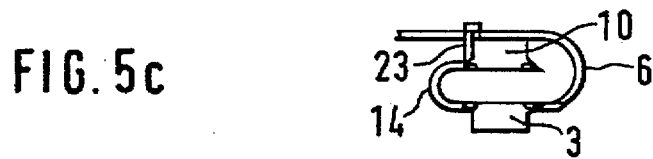

FIG. 5 is an illustration of another embodiment with locking connections; in FIGS. 5a and 5b is shown a support body 1 in the folded up state with differently designed locking openings 22. As shown by the side view of FIG. 5c, a detent 23 on the upper fastening 10 engages said openings.

All the support bodies 1 described in the aforementioned embodiments are, as stated, so preshaped by the curved web 14 that the fastenings are directly superimposed. The material used is silicone, which on the one hand ensures a good skin compatibility and on the other has a favourable effect on the fixing of the clip to the fastening even when there are different frictional and/or clamping connections. The part is constructed in one piece and can therefore be manufactured inexpensively by injection moulding.

I claim:

1. A pulsoximetry sensor comprising:

a support body including two fastenings;

an arcuate elastic web interconnecting the two fastenings of the support body so that the two fastenings are adapted to be positioned on the opposite sides of a hand or a foot when the support body is fixed to the hand or foot; and first and second sensor elements, each of which is located in a depression of a respective one of the two fastenings so that the sensor elements are retained opposite one another, wherein the support body is adapted to be fixed to the body part by means of a flexible clip shaped onto the first fastening and which is oriented in the same direction as the web, so that the support body is adapted to be laterally engaged on the foot or hand and is held by the clip, which is guided via the second fastening and which spans the foot or hand.

2. A pulsoximetry sensor according to claim 1, wherein on top of one of the fastenings is provided at least one recess for receiving the clip and for holding the clip in its position.

3. A pulsoximetry sensor according to claim 2, wherein on top of one of the fastenings are provided two displaced recesses each having two facing edges, the recesses and facing edges interacting with the clip to hold the clip in position by a clamping action.

4. A pulsoximetry sensor according to claim 2, wherein the recess has a dove-tail cross-section.

5. A pulsoximetry sensor according to claim 4, wherein the clip has lateral corrugation.

6. A pulsoximetry sensor according to claim 1, wherein the clip has corrugations on top and/or bottom corrugations and is guided on the edge of the depression by at least one ring holding the clip in position.

7. A pulsoximetry sensor according to claim 1, wherein on the fastening or on the web is provided a detent in which the clip engages with corresponding locking openings.

8. A pulsoximetry sensor according to claim 7, wherein the support body is made from silicone.

9. A pulsoximetry sensor according to claim 3, wherein the recess has a dove-tail cross-section.

10. A pulsoximetry sensor according to claim 1, wherein the clip has lateral corrugation.

11. A pulsoximetry sensor according to claim 5, wherein the support body is made from silicone.

12. A pulsoximetry sensor according to claim 1, wherein the support body is made from silicone.

* * * * *